(12) United States Patent
DiBello et al.

(10) Patent No.: US 7,854,393 B2
(45) Date of Patent: Dec. 21, 2010

(54) AIR FRESHENER

(75) Inventors: Anna DiBello, Homebush (AU); Mark Armstrong, Yowie Bay (AU); Henri Spaile, Surry Hills (AU); David Petarcic, Hebersham (AU); Ed Kopinski, Edensor Park (AU)

(73) Assignee: Ashland Licensing and Intellectual Property, LLC, Dublin, OH (US)

( * ) Notice: Subject to any disclaimer, the term of this patent is extended or adjusted under 35 U.S.C. 154(b) by 142 days.

(21) Appl. No.: 11/595,387

(22) Filed: Nov. 9, 2006

(65) Prior Publication Data
US 2007/0119963 A1    May 31, 2007

Related U.S. Application Data

(60) Provisional application No. 60/734,848, filed on Nov. 9, 2005.

(51) Int. Cl.
*A61L 9/04* (2006.01)

(52) U.S. Cl. .............................. 239/34; 239/44; 239/47; 239/57

(58) Field of Classification Search ................... 239/34, 239/44, 47, 57, 58, 59
See application file for complete search history.

(56) References Cited

U.S. PATENT DOCUMENTS

| | | | | |
|---|---|---|---|---|
| 3,257,077 A | * | 6/1966 | Corning | 239/47 |
| 4,523,870 A | | 6/1985 | Spector | |
| 4,732,321 A | * | 3/1988 | Dolan | 239/45 |
| 4,840,773 A | * | 6/1989 | Wade | 422/124 |
| 4,950,457 A | | 8/1990 | Weick | |
| 5,222,186 A | * | 6/1993 | Schimanski et al. | 392/395 |
| 5,603,455 A | | 2/1997 | Lin | |
| 5,647,053 A | * | 7/1997 | Schroeder et al. | 392/390 |
| 5,762,549 A | | 6/1998 | Scheuer et al. | |
| D398,047 S | | 9/1998 | Chen | |
| 5,820,792 A | | 10/1998 | Lin | |
| 5,865,372 A | * | 2/1999 | Ceresko | 239/60 |
| 5,932,147 A | | 8/1999 | Chen | |
| D419,659 S | | 1/2000 | Yang | |
| 6,264,887 B1 | | 7/2001 | Farmer | |

(Continued)

FOREIGN PATENT DOCUMENTS

EP    1 031 446    8/2000

(Continued)

*Primary Examiner*—Len Tran
*Assistant Examiner*—Trevor E McGraw
(74) *Attorney, Agent, or Firm*—Wood, Herron & Evans, LLP

(57) ABSTRACT

A clip on type air freshener device having a housing with openings in walls thereof permitting air flow through a cavity in the housing. A bottle that holds a supply of fragrance bearing liquid is mounted on the housing and has a wick with a portion thereof projecting into the cavity in the housing. An open ended sleeve is mounted on housing in axial alignment with such projecting wick portion and is adjustably moveable axially along the wick selectively in one position to completely cover the wick projecting portion and in another position leave at least a major portion thereof exposed to air flow through said housing openings. The wick cover is exposed through an opening in the housing giving the user a visual indication as to the amount of wick exposed for evaporation of the fragrance during usage of the device.

9 Claims, 4 Drawing Sheets

U.S. PATENT DOCUMENTS

| | | |
|---|---|---|
| D452,955 S | 1/2002 | Bulsink |
| D465,019 S | 10/2002 | Wu |
| 6,514,467 B1 * | 2/2003 | Bulsink et al. ............... 422/122 |
| D474,268 S | 5/2003 | Choke-arpornchai et al. |
| D480,792 S | 10/2003 | Millan |
| D485,340 S | 1/2004 | Wu |
| D485,341 S | 1/2004 | Wu |
| D487,144 S | 2/2004 | Choke-arpornchai et al. |
| 6,782,194 B2 | 8/2004 | Schneiderbauer |
| 6,862,403 B2 * | 3/2005 | Pedrotti et al. ............. 392/395 |
| 7,025,283 B2 * | 4/2006 | Torres ......................... 239/34 |
| 7,140,553 B2 * | 11/2006 | Zobele ........................ 239/34 |
| 7,243,859 B2 * | 7/2007 | Caserta et al. ................ 239/34 |
| 2003/0007787 A1 | 1/2003 | Rymer |
| 2003/0175171 A1 | 9/2003 | Yamamoto et al. |
| 2003/0175172 A1 | 9/2003 | Altmann |
| 2003/0180194 A1 * | 9/2003 | Massimo .................... 422/124 |
| 2004/0129742 A1 * | 7/2004 | Torres ......................... 223/34 |
| 2004/0262420 A1 * | 12/2004 | Hansen et al. ................ 239/44 |
| 2004/0263343 A1 | 12/2004 | Seresini |
| 2005/0001053 A1 * | 1/2005 | Zobele ......................... 239/44 |
| 2005/0002834 A1 | 1/2005 | Gohil |
| 2005/0053528 A1 | 3/2005 | Rymer |
| 2005/0104236 A1 | 5/2005 | Chen |
| 2005/0127538 A1 | 6/2005 | Fabrega et al. |
| 2007/0001025 A1 * | 1/2007 | Caserta et al. ................ 239/59 |
| 2007/0057084 A1 * | 3/2007 | Vieira ......................... 239/34 |

FOREIGN PATENT DOCUMENTS

| | | |
|---|---|---|
| FR | 2 756 184 | 5/1998 |
| GB | 2 392 841 | 3/2004 |
| WO | WO 2004/091673 | 10/2004 |

* cited by examiner

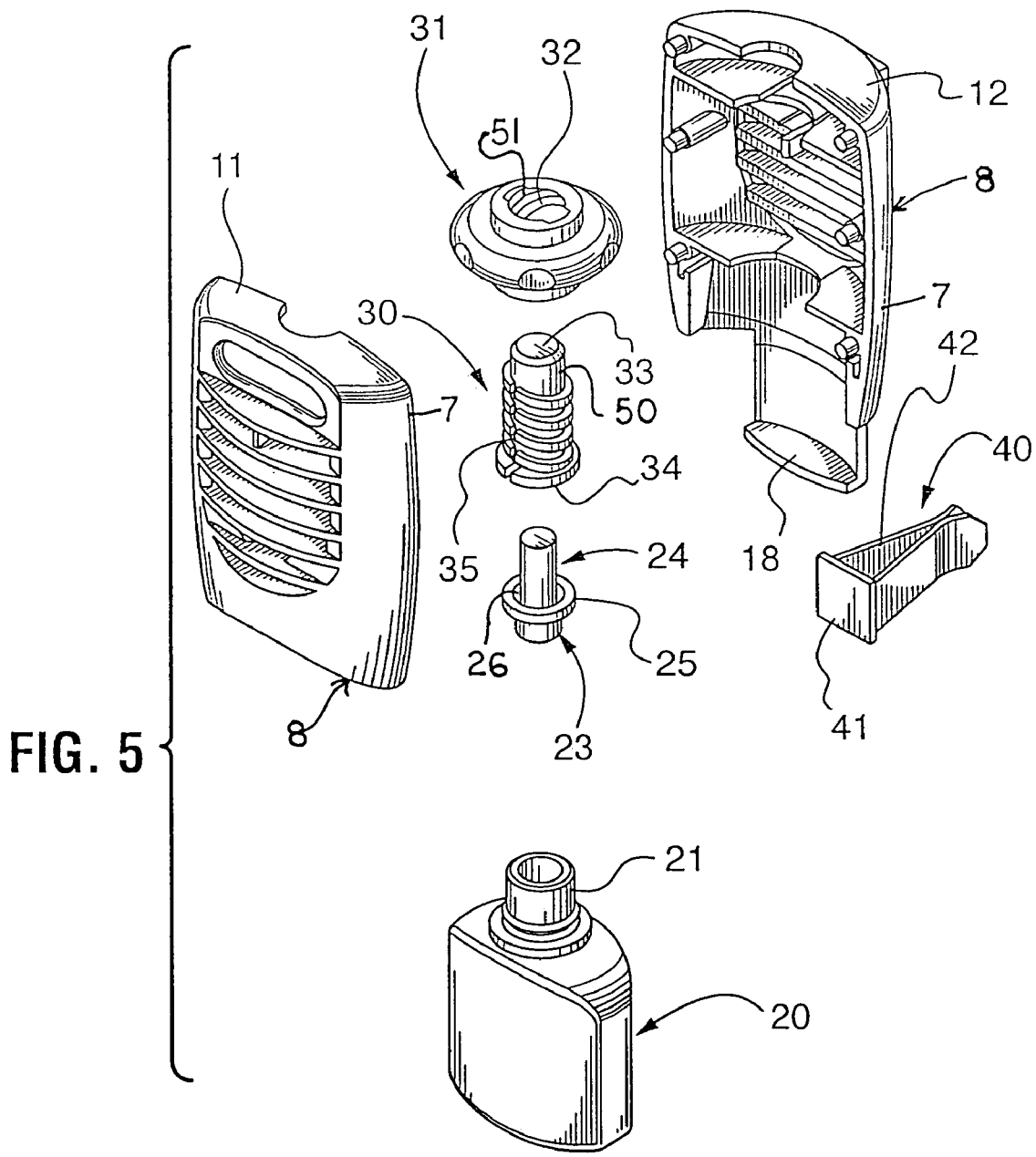

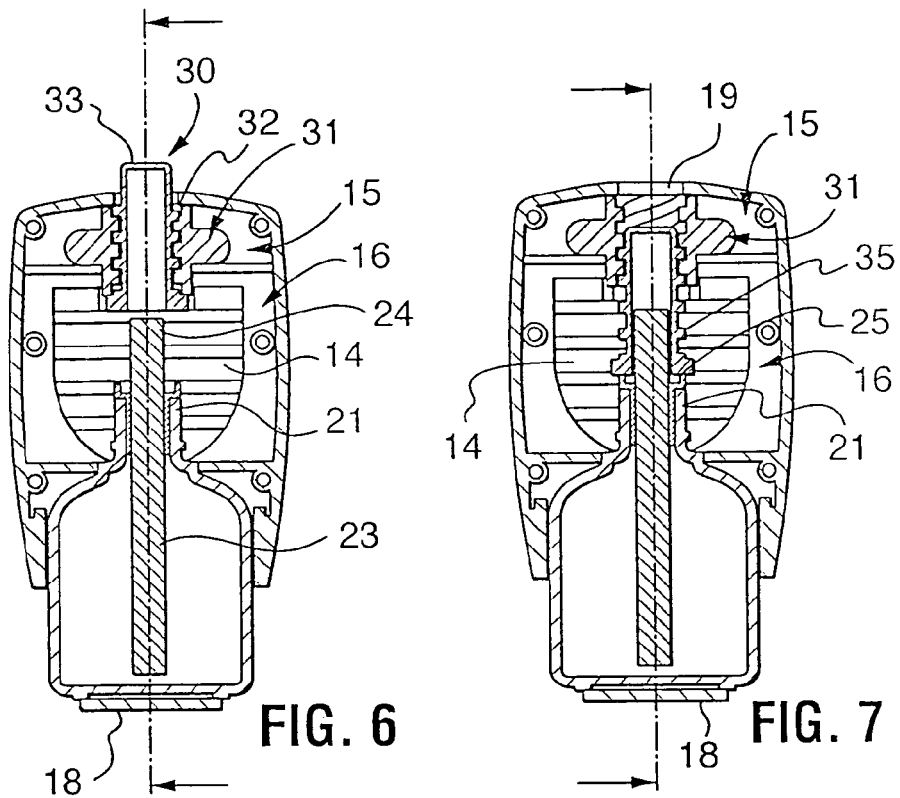
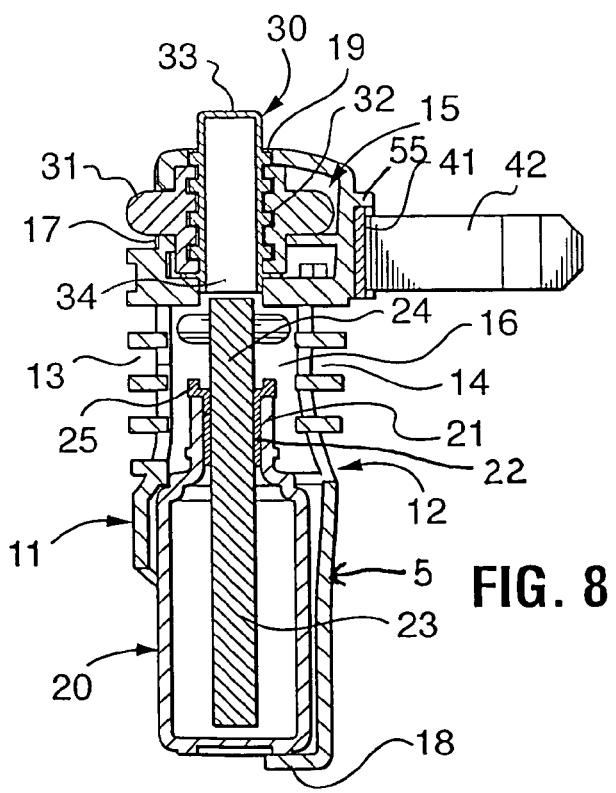

AIR FRESHENER

This application claims priority from U.S. Provisional Application Ser. No. 60/734,848 filed on Nov. 9, 2005 which is incorporated by reference herein.

BACKGROUND OF THE INVENTION

1. Field of Invention

This invention relates generally to air fresheners and more particularly to a small clip on type primarily intended for use in automobiles.

2. Description of the Prior Art

Clip on automobile air freshener units are many and varied and commonly attach in some convenient manner to the grill at the outlet of a forced air system or HVAC (e.g. air conditioning system) in the cabin of a motor vehicle. Many of the known devices fail to regulate and/or control discharge of the fragrance and/or maintain a seal tight enclosure for the volatile liquid/fragrance during non use and thus have a life span highly based on time rather than usage.

Examples of known air freshener units are illustrated in the following US design patents assigned to Aromate Industries Co., Ltd.: Design Pat. D465,019 granted Oct. 29, 2002 and entitled Automobile Air Freshener Assembly; Design Pat. D485,341 granted Jan. 13, 2004 and entitled Clip-On Air Freshener Assembly; and Design Pat. D485,340 granted Jan. 13, 2004 entitled Combined Automobile Freshener and Fan Assembly.

The foregoing design patents, D465,019 and D485,341, each disclose a two part housing with a lip on the lower end thereof for detachably retaining therein a bottle and a clip projecting from the rear face of the housing for clipping the device onto presumably the grill of an automobile air conditioning system. The housing has openings in the front and rear face thereof that presumably align with a wick projecting from the bottle.

The device illustrated in the D485,340 patent further incorporates therein a power driven fan.

Further examples of motor vehicle air freshener devices are found in the following: U.S. Pat. No. 4,523,870 granted Jun. 18, 1985 to Donald Spector, U.S. Pat. No. 6,514,467 granted Feb. 4, 2003 to D. J. Buisink et al., U.S. Pat. No. 6,782,194 granted Aug. 24, 2004 to L. Schneiderbauer, and U.S. Patent Application 2003/0007787 published Jan. 9, 2003 entitled Evaporator Device to S. Rymer.

Of the foregoing references, U.S. Pat. No. 6,514,467 is considered the most closely related to the present device in that it includes a wick cover that is movable back and forth axially along the exposed diffusing portion of the wick. The cover however is not exposed through an opening in the housing and therefore does not give to the user any visual indication of the amount of wick exposed to air flowing through the device during usage of the same. Also the drive for moving the cover differs and there is no groove in the wick supporting collar to ensure a good seal that prevents leakage during non use of the device.

SUMMARY OF INVENTION

The present invention provides a clip on type air freshener device having a housing with openings in walls thereof permitting air flow through a cavity in the housing. A bottle that holds a supply of fragrance bearing liquid is mounted on the housing and has a wick with a portion thereof projecting into the cavity in the housing. An open ended sleeve is mounted on housing in axial alignment with such projecting wick portion and is adjustably moveable axially along the wick selectively in one position to completely cover the wick projecting portion and in another position leave at least a major portion thereof exposed to air flow through said housing openings. The wick cover is exposed through an opening in the housing giving the user a visual indication as to the amount of wick exposed for evaporation of the fragrance during usage of the device.

A principle object of the present invention is to provide a clip on type air freshener unit that has a simple and effective means to control exposure of the fragrance transfer area i.e. diffuser part of the device and thus regulate the rate of evaporation.

A further object of the present invention is to provide the forging unit and which further has means visually to indicate the amount of wick exposed to ambient in the diffuser part of the device.

In keeping with the foregoing, there is provided in accordance with one aspect of the present invention a clip on type air freshener device comprising a housing having openings in walls thereof permitting air flow through a cavity in the housing. A bottle is used for holding a supply of fragrance bearing liquid. A wick projects into such liquid in the bottle and having a portion thereof projecting though and beyond an open ended neck on the bottle. The wick projecting portion is disposed in the housing cavity. A wick cover comprising an open ended sleeve is movably mounted on the housing for movement axially along the projecting wick portion selectively in one position to completely cover the wick projecting portion and in another position to leave at least a major portion of the wick projecting portion exposed to air flow through the housing cavity via the openings. Means for moving the wick cover comprises a finger engageable movable member having a cam surface thereon, movable along a circular path about the longitudinal axis of the wick and engaging a cam follower on the sleeve.

There is also provided in accordance with the present invention a clip on type air freshener device for use in an automobile, the device comprising a housing having openings in walls thereof permitting air flow through a cavity in the housing and a bottle for holding a supply of fragrance bearing liquid. A wick projects though an open ended neck on the bottle into such liquid in the bottle and has a portion projecting upwardly beyond the bottle neck. The wick projecting portion is disposed in the housing cavity. A wick cover comprises a sleeve open at one end to receive the wick projecting portion and closed at the opposite end. The sleeve is movably mounted on the housing and disposed in axial alignment with the projecting wick portion for movement axially along the wick projecting portion. In a first position the sleeve completely covers the wick projecting portion and in a second position opposite the first position, the sleeve leaves at least a major portion of the projecting wick portion exposed to air flow through the cavity in the housing via the openings therein and an opening in the housing disposed in axial alignment with the sleeve. The opening in the housing exposes to view an upper end portion of the sleeve thereby giving a visual indication of the amount of wick being exposed during use of the device.

These an other objects and features of the invention will become apparent to those skilled in the art from the following detailed description and appended claims.

BRIEF DESCRIPTION OF THE DRAWINGS

A better understanding of the present invention will be had upon reference to the following description in conjunction with the accompanying drawings in which like numerals refer to like parts throughout the several views and wherein:

FIG. 5 is an oblique exploded view of the air freshener unit shown in FIG. 1;

FIG. 6 is a sectional views of the air freshener unit of FIG. 1 taken along line 6-6 of FIG. 4 showing the fragrance dissipating portion of the device respectively in a fully open and a closed position;

FIG. 7 is a sectional views of the air freshener device taken along line 6-6 of FIG. 4 showing the fragrance dissipating portion of the device respectively in a fully open and a closed position;

FIG. 8 is sectional view of the air freshener unit taken along line 8-8 of FIG. 4.

DESCRIPTION OF PREFERRED EMBODIMENT

Figure 1:
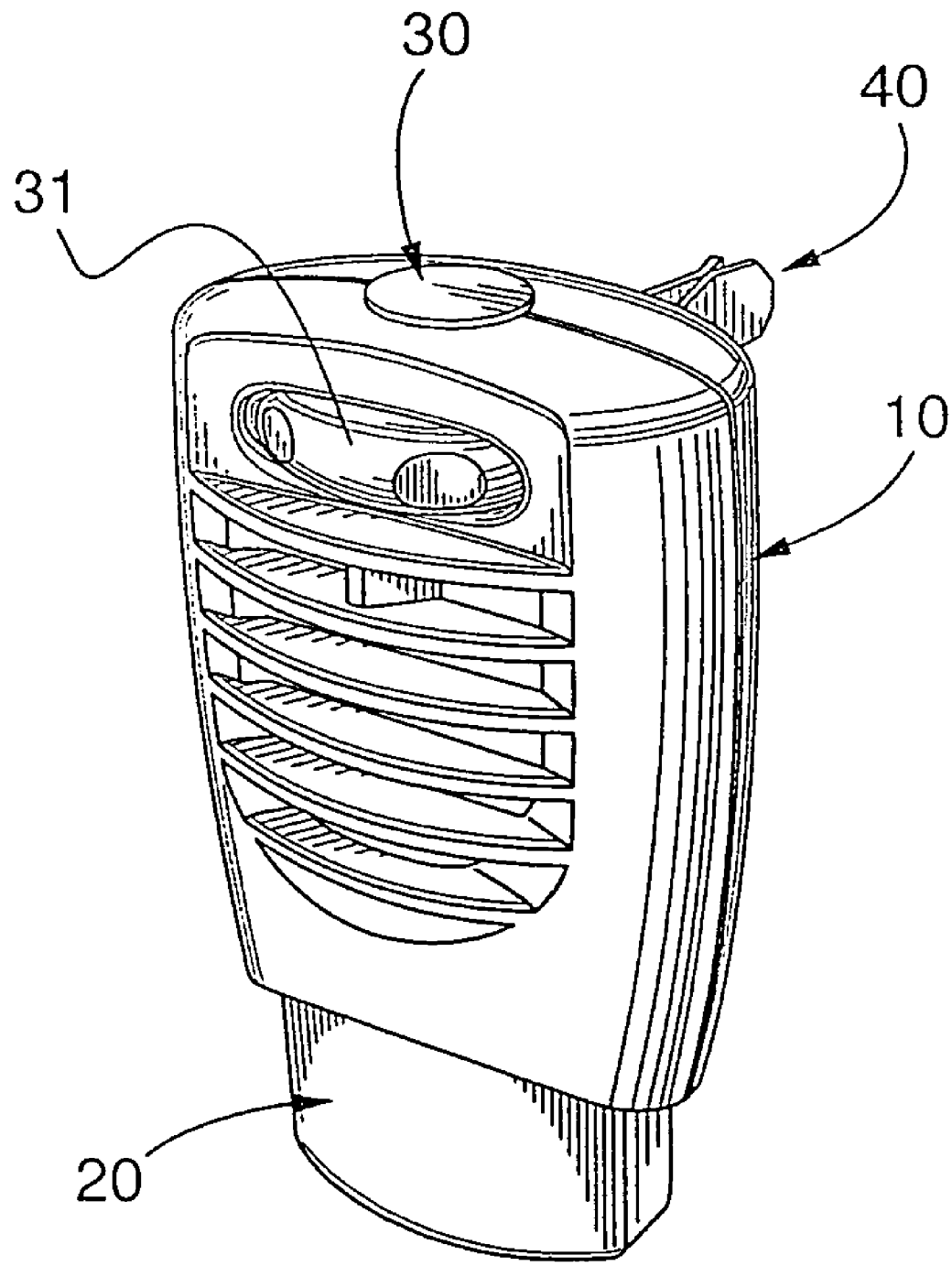
FIG. 1 is an oblique view of the air freshener unit provided in accordance with the present invention.
Figures 2, 3:
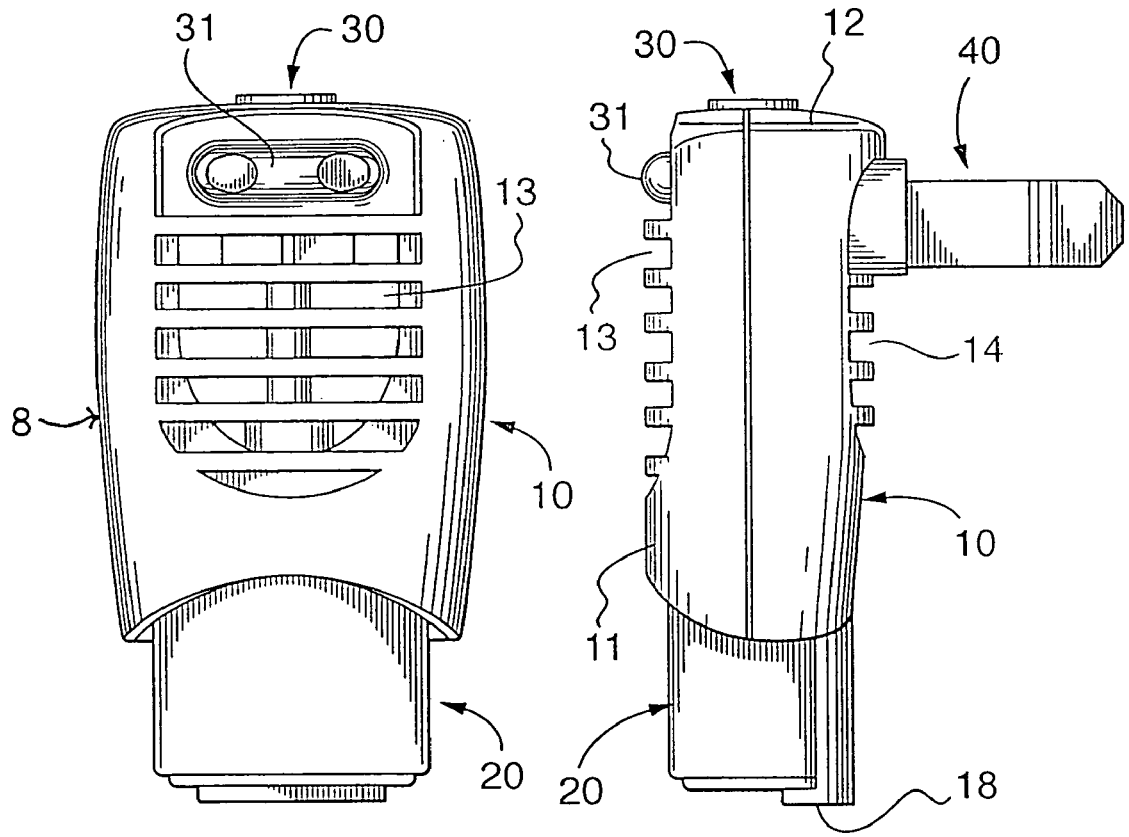
FIG. 2 is a front view of the air freshener unit shown in FIG. 1.
FIG. 3 is a left side view of the air freshener unit shown in FIG. 1.
Figure 4:
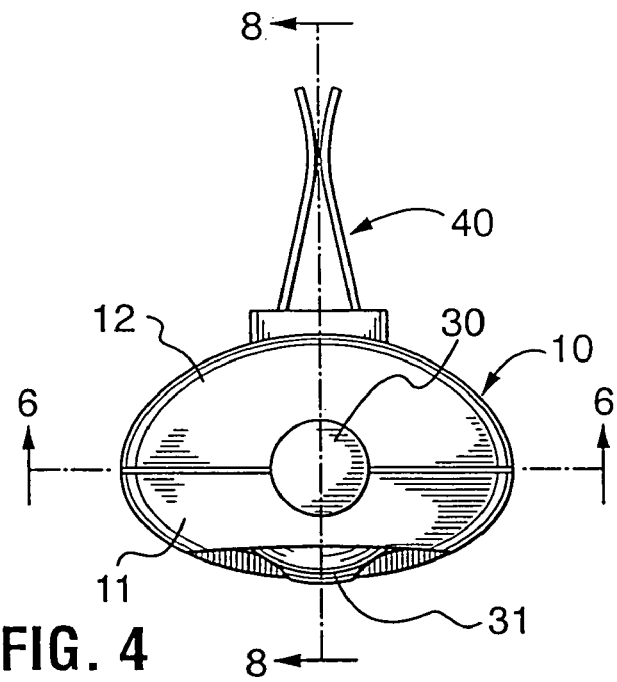
FIG. 4 is a top view of the air freshener unit shown in FIG. 1.

Illustrated in the drawings is an air freshener unit comprising a housing 10, a bottle 20 having a wick that projects therefrom into the housing and a wick cover 30 that is adjustably movable from one position to another where in one position the projecting portion of the wick is completely covered and in the other position at least a major portion of the projecting wick portion is uncovered. A vent attachment clip 40 projects from the rear face of the housing.

The housing 8 has respective front and rear molded portions 11, 12 suitably permanently joined together as for example by fusion or heat bonding depending upon the plastics material used, by adhesive or by cooperating lugs providing a snap fit. The latter, if desired, can provide a detachable interconnection of the body portions 11, 12. The front and rear body portions of the housing 8 have respective large air flow openings 13, 14 that are disposed generally in alignment. The front and rear housing portions 7 have respective recessed portions disposed in face-to-face relation and together provide a first cavity 15, (see FIGS. 6, 7, and 8), that captively retains therein a wheel nut 31. The wheel nut 31 has a finger engageable portion projecting through an opening 17 in the front face of the housing. Adjacently disposed further recessed portions provide a second cavity 16 through which air flows via aligned openings 13, 14 into and out of the housing 8.

The rear housing portion 12 has a flange 18 projecting from the lower end which provides a bottle support ledge or retention clip 5. The bottle 20 rests on this ledge and if desired can be releasibly retained thereby for reuse of the housing with a replacement bottle of fragrant material. The bottle has an open ended neck portion 21 that projects into the housing second cavity 16.

A wick passes through a collar 22 that press fits into (or onto if desired) the neck of the bottle. The wick has a portion 23 that extends into the bottle and a portion 24 that projects from the bottle neck through the second housing cavity 16 in a direction toward the housing first cavity 15 and in axial alignment with a threaded through hole 32 in the wheel nut 31. The collar has an outwardly directed flange 25 in which there is located annular groove 26.

The wick cover 30 comprises an elongate sleeve 50 having a closed upper end 33 and an open lower end 34 that is disposed in axial alignment with the exposed wick projecting end portion 24. On the outer surface of the sleeve 50 there are threads 35 that mate and cooperatively engage threads 51 formed in the wheel nut 31 and are threaded through hole 32 in the wheel nut 31. Rotation of the wheel nut 31, that is held captive in the housing 8 except for the permitted rotational movement, causes the wick cover's open end to move in a direction toward and away from the flange 25 on the collar 22. The amount of travel is such as to enable completely covering the wick projecting portion 24 when in one extreme position (closed position) and in another opposite extreme position (open position) leave at least substantially all of that projecting wick portion exposed. In the closed position the sleeve lower open end 34 can if desired project into the annular groove 26 in the upper surface portion of the flange 25 for a tight sealing engagement thereby ensuring minimum or non leakage during non use of the device.

The threads 51 on the wheel nut 31 constitute a cam surface and the threads 35 on the sleeve 50 a cam follower. A simpler arrangement if desired could be provided in place of the continuous threads illustrated to perform the same function.

The housing 10 has an opening 19 in the upper end thereof through which an end portion of the sleeve 30 can project. The amount by which the sleeve 50 projects from the housing 10, (or alternatively the depth of the opening to the top closed end of the sleeve), gives a visual indication to the user as to how much of the wick projecting portion is exposed for transferring fragrance vapors to air flowing through the housing cavity via openings 14, 13 during use of the device. The fully open and fully closed positions are clearly illustrated respectively in FIGS. 6, 8, and FIG. 7.

The mounting clip 40 has a base 41 and more particularly a square base from which a pair of prongs 42 project. The base has a peripheral portion that projects beyond the base end of the prongs and such peripheral portion slip fits between a spaced apart pair of L-shaped flanges on the rear face of the housing 10. The square base enables the clip to be positioned as shown in the drawings for fitting onto a grill with vertical bars or rotated 90 degrees from that position for fitting onto a grill having horizontal bars. The upper edge of the base 41 engages a ledge 55 projecting from the rear face of the housing as best illustrated in FIG. 8). The mounting clip 40 may also be formed having prongs 42 including a plurality of ridges forming teeth to aid in gripping to a holding member.

The foregoing detailed description is given primarily for clearness of understanding and no unnecessary limitations are to be understood therefrom, for modification will become obvious to those skilled in the art upon reading this disclosure and may be made upon departing from the spirit of the invention and scope of the appended claims. Accordingly, this invention is not intended to be limited by the specific exemplifications presented herein above. Rather, what is intended to be covered is within the spirit and scope of the appended claims.

We claim:

1. A clip on type air freshener device comprising:
a housing having openings in walls thereof permitting air flow through a cavity in the housing,
a bottle for holding a supply of fragrance bearing liquid,
a wick projecting into such liquid in the bottle and having a portion of thereof projecting through and beyond an open ended neck on the bottle, said wick projecting portion being disposed in said housing cavity and having an axis coincident with the length of the wick,
a wick cover comprising an open ended sleeve having an axis aligned with the axis of the wick projecting portion and movably mounted on said housing for movement in a direction toward and away from the open ended neck on the bottle along the length of the axis of said wick projecting portion selectively in a first position to completely cover said wick projecting portion and in a second position to leave at least a portion of said wick projecting portion exposed to air flow through said housing cavity via said openings, a finger engageable member having a hole, said hole aligned with the axis of the sleeve and with a cam surface therethrough for moving said wick cover, the finger engageable member being movable along a circular path about the axis of the sleeve and engaging a cam follower on said sleeve, wherein an end of said sleeve passes through said hole, and an opening in an upper end wall of said housing, said opening axially aligned with said hole in the finger engageable member, wherein an end of the sleeve passes through said hole in said finger engageable member and said opening thereby exposing to view an upper end portion of the sleeve outside of said housing and thereby visually indicating the amount of wick exposed during use of the device.

2. The device as defined in claim 1 wherein said wick is mounted in a collar that press fits into the neck of said bottle and wherein the open end of the sleeve is in close abutting relation with said collar when said sleeve is in said first position.

3. The device as defined in claim 2 including an annular groove in an end of said collar when said sleeve is in said second position and wherein said sleeve projects into said groove when said sleeve is in said first position.

4. The device as defined in claim 3 including a flange extending outwardly from said collar that is engageable with an end portion of said bottle neck and wherein said annular groove is located in said flange.

5. A clip on type air freshener device for use in an automobile, said device comprising:

a housing having openings in walls thereof permitting air flow through a cavity in the housing, a bottle for holding a supply of fragrance bearing liquid, a wick projecting through an open ended neck on the bottle into such liquid in the bottle and having a portion projecting upwardly beyond said bottle neck, said wick projecting portion being disposed in said housing cavity and having an axis coincident with the length of the wick, a wick cover comprising an elongated sleeve having an axis aligned with the axis of the wick projecting portion, the sleeve being open at one end thereof to receive said wick projecting portion and closed at the opposite end, said sleeve being mounted on said housing in alignment with the axis of said wick projecting portion, and moveable in a direction toward and away from the open ended neck on the bottle along the length of the axis of said wick projecting portion from one position to another of a first position in which said wick projecting portion is completely covered and a second position in which at least a part of said wick projecting portion is exposed to air flow through said cavity in said housing via the openings therein, and an opening in an upper end wall of said housing, said opening axially aligned with said sleeve so that an upper end portion of said sleeve projects through said opening in said second position, thereby exposing to view the upper end portion of the sleeve outside of said housing, thereby visually indicating the amount of wick exposed during use of the device.

6. The device as defined in claim 5 including finger engageable means mounted on said housing and operatively associated with said sleeve for moving the same from one to the other of said first and second positions.

7. The device as defined in claim 6 wherein said finger engageable means is mounted on said housing for rotational movement about the axis of said sleeve.

8. The device as defined in claim 7 wherein said finger engageable means comprises a wheel nut threadingly engaging threads on the external surface of said sleeve and means preventing movement of said wheel nut in a direction along the axis of said sleeve.

9. The device as defined in claim 8 wherein said wheel nut is located in a second cavity in said housing.

* * * * *